United States Patent [19]

Steinman

[11] Patent Number: 4,761,369

[45] Date of Patent: Aug. 2, 1988

[54] PROCESS FOR MEASURING CALCIUM LEVELS IN BIOLOGICAL FLUIDS

[75] Inventor: Gary D. Steinman, Flushing, N.Y.

[73] Assignee: David Diagnostics, Inc., Astoria, N.Y.

[21] Appl. No.: 862,479

[22] Filed: May 12, 1986

[51] Int. Cl.$^4$ .............................................. C12Q 1/58
[52] U.S. Cl. ............................................. 435/19; 435/4
[58] Field of Search ............................................ 435/19

[56] References Cited

U.S. PATENT DOCUMENTS

| | | | |
|---|---|---|---|
| 4,140,579 | 2/1979 | Moncla | 435/19 |
| 4,168,203 | 9/1979 | Takahashi | 435/19 |
| 4,657,854 | 4/1987 | Wegfahrt | 435/14 |

Primary Examiner—Sam Rosen

[57] ABSTRACT

A process for measuring the calcium concentration of a biological fluid is carried out by fixing the amounts of phospholipase A2 (PLA) and phosphatidylcholine (PC), in the presence of a buffer and a detergent such as sodium deoxycholate, in enzymatic Reaction I,

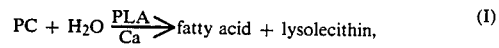

and measuring the rate of appearance of the products so that the rate of reaction of PLA can be determined. The reaction rate of this enzyme is directly proportional to the level of calcium present. The calcium concentration of the biological fluid being tested is quantitatively determined by comparing the reaction rate of pohospholipase A2 to a standard of known calcium concentration. Preferably, the reaction rate of porcine pancreas phospholipase A2 is measured by determining the amount of lysolecithin produced in Reaction I by comparison of the optical density of the resultant color of coupled Reactions II and III,

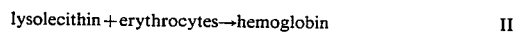

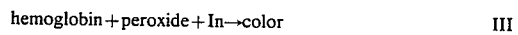

wherein In is a colorimetric oxidation indicator, against at least one colorimetric standard of known calcium concentration. A paper phase procedure for determining calcium levels in biological fliuds is also provided.

11 Claims, No Drawings

PROCESS FOR MEASURING CALCIUM LEVELS IN BIOLOGICAL FLUIDS

This invention relates to a chemical process for the measurement of calcium in biological fluids, such as urine or blood. More particularly, it relates to an enzyme reaction that is calcium-dependent in a quantitative fashion.

The inportance of being able to accurately measure levels of calcium is well known. Calcium is the fifth most common element in the body. Various conditions are encountered whereby the blood serum level of calcium is elevated or depressed. Excess calcium can be found in hyperparathyroidism and hypercalcemia of malignancy. On the other hand, depressed levels are seen with vitamin D deficiency and renal failure.

Calcium in biological fluids has traditionally been difficult to measure accurately and precisely. The most commonly employed techniques today are atomic absorption spectrophotometry, ion-selective electrode potentiometry, and calcium-dye complex colorimetry. These methods require sophisticated analytical equipment, precise manipulation, and technical expertise. A critical need exists for a simple, accurate and inexpensive method applicable for use in the physician's office or even within a patient's home to specifically determine calcium levels in biological systems.

Accordingly, it is an object of the present invention to provide an accurate, yet inexpensive, method to determine calcium levels in biological fluids. An invention to provide such a method should be executed in a paper-phase procedure, which is particularly economical since the use of minute amounts of premeasured reagents is possible, as well as in a solution phase. A further object of the invention is to provide a method that may be readily adaptable to existing and widely available instrumentation, thereby further allowing for economical and convenient use.

Certain of the foregoing and related objectives are readily attained by utilizing the absolute calcium dependence of phospholipase A2 of porcine pancreas (EC 3.1.14). While the chemistry of this enzyme is known, there appears to have been no attempt to utilize its calcium-dependency in a quantitative analytical fashion, let alone employ this property to measure calcium levels in biological systems. (G. H. De Haas, et al., Biochim. Biophys. Acta, 159, 103 (1968); 239, 252 (1971).) It has been the general practice of biochemists to add excess calcium to systems designed to evaluate and utilize phospholipase from various sources. ("Enzymes and Related Biochemicals", Worthington, Freehold, NJ, 1982, p. 158.) Thus, the prior art, by directing the use of saturating amounts of calcium, teaches away from the methodology of the present invention. Furthermore, in the 18 years since the original observation, no apparent attempt has been made to apply such a principle in the quantitative determination of calcium in biological systems (N. W. Tietz, ed., "Textbook of Clinical Chemistry", W. B. Saunders, Philadelphia, 1986, p. 1342).

Phosphoplipase A2 (PLA) specifically cleaves the middle fatty acid off phosphatidylcholine (PC) to yield lysolecithin, a potent hemolytic agent.

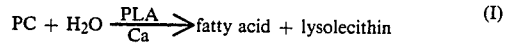

$$PC + H_2O \xrightarrow[Ca]{PLA} \text{fatty acid} + \text{lysolecithin} \quad (I)$$

The phospholipase activity is greatest at pH 8.0. The equilibrium of the hydrolytic reaction using this enzyme is shifted toward the two products in the presence of calcium. This is due to the fact that PLA absolutely requires the presence of calcium as a cofactor to be activated and to function maximally. By using a predetermined amount of PC and PLA, and measuring by some means the appearance of products, one may determine the degree of activation of PLA, the enzyme catalyst. The extent of reaction, i.e., the activity of this enzyme, is directly proportional to the calcium concentration. Sodium deoxycholate (or similar detergent) is added to aid in emulsifying the lecithin (PC) reactant. Most importantly, however, is that the calcium dependency of this enzymatic reaction does not extend to chemically similar substances likely to be found in biological systems, e.g., divalent cations such as magnesium.

In principle, the fatty acid product can be quantitated by titration. The decrease in acyl ester bonds can be followed by reaction with hydroxylamine. The decrease in the turbidity created by the lecithin (PC) reactant is a measure of the clearing effect of the lysolecithin product.

A preferred mode for quantitatively determining the reaction products of Reaction I, however, takes advantage of the hemolytic effect of the lysolecithin product.

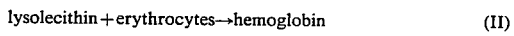

$$\text{lysolecithin} + \text{erythrocytes} \rightarrow \text{hemoglobin} \quad (II)$$

The hemoglobin (Hgb) released from intact erythrocytes attacked by the lysolecithin can be measured by various reactions such as with ferricyanide (W. Neumann & E. Habermann, Hoppe Seiler's F. Physiolog. Chem., 296, 166 (1964)). Alternatively, advantage can be taken of the peroxidase-like activity of hemoglobin. The color change of benzidine and related oxidation indicators (In) in the presence of a peroxide (e.g., $H_2O_2$) has been effectively used commercially in various hemoglobin detection tests both in solution and in the paper phase (e.g., Ames "Hemastix").

$$Hgb + H_2O_2 + In \rightarrow \text{color} \quad (III)$$

Thus, the amount of color produced in Reaction III is directly proportional to the concentration of calcium in the original sample.

In summary, the lysolecithin produced in Reaction I is reacted with erythrocytes (Reaction II). The hemoblogin released, in turn, catalyzes the transfer of oxygen from a peroxide to an indicator in Reaction III. A color is produced whose intensity is proportional to the calcium concentration in the original sample in Reaction I. The calcium concentration is determined through the specific colorimetric reaction by comparison with one or more known standards. The optical density of the resultant color produced, as a function of time, is directly proportional with the concentration of the calcium.

For Reaction III, examples of indicators known to be suitable to quantitatively measure peroxide in the presence of a peroxidase are pyrogallol, iodide, 4-aminoantipyrine+N,N-dimethylaniline, 4-aminoantipyrine+2,4-dichlorophenolsulfonic acid, benzidone, tetramethylbenzidine, and o-tolidine, among others.

The method is so designed that the erythrocytes in Reaction II can come from exogenous sources or from the cellular fraction of the whole blood specimen being tested. PLA is available commercially from bee venom, procine pancreas, and snake venom.

The inventive process may be employed in the form of an aqueous solution or in a paper phase, the latter being especially economical and practicable for in-home or in-office use. In solution phase, the final optical density of the solution is, preferably, measured in a spectrophotometer. For use in the paper phase, the reagents strips are prepared in such a way that the initial erythrocytes are separated from the final reagents, so that only the released hemoglobin is detected by the indicator. It is known, e.g., U.S. Pat. Nos. 3,092,465, and 3,298,789, that cells can be separated from serun in a paper phase test by applying a layer of various cellulose derivatives to the paper.

In the following, an example of a typical format which can be used to measure the calcium in test samples will be more fully described. However, it should be noted that this example is given only by way of illustration and not limitation.

EXAMPLE

A standard source of erythrocytes is prepared by washing the cells of a fresh sample of heparinized whole blood four times with normal saline. Following the final centrifugation, 0.025 ml of packed erythrocytes is suspended in 8 ml of normal saline ("RBC"). Egg yolk lecithin emulsion is prepared by diluting 1 volume of phosphatidylcholine solution (100 mg/ml Ethanol) with 9 volumes of absolute methanol and then adding 10 volumes 1/15M phosphate buffer (pH 8.0) containing sodium deoxycholate (5 mg/ml). A total of 125 units of phospholipase A2 (PLA) from porcine pancreas is dissolved in 1 ml of 1/15M phosphate buffer (pH 8.0). To 0.5 ml of test sample is added 1.4 ml "RBC" suspension, 0.1 ml lecithin emulsion, and 0.025 ml PLA solution with stirring. After 3 minutes incubation at room temperature, the mixture is centrifuged for 1 minute. To 0.05 ml of the resultant supernatant is added 0.05 ml TMBZ (4 mg tetramethylbenzidine in 1 ml absolute methanol) and 0.1 ml 3% $H_2O_2$. One minute later, 3 ml of 0.4N HCl is added with stirring and the optical density is read at 450 nm against a water blank and correlated with solutions of known calcium concentration. Alternatively, distilled water can replace HCl in the final step, and in this case the optical density is read at 655 nm. Longer incubation times give proportionally higher optical densities.

A variation of this method would be to impregnate a piece of filter paper or a swab with a solution of TMBZ and a peroxide, followed by air-drying. Above this would be placed a piece of filter paper impregnated with PLA, lecithin, deoxycholate, and phosphate buffer, and similarly air-dried. Between the two layers would be sandwiched a membrane, such as from one of the cellulose derivatives, which would be permeable to free diffusing hemoglobin but not whole red blood cells. Erythrocytes would be supplied to the upper layer exogenously or from a whole blood sample. If plasma or serum is being tested, the sample is applied directly to the upper (PLA) layer and the color resulting in the lower (TMBZ) layer would be read against a color standard chart, with a reflectance spectrophotometer, or in comparison with standard samples run in parallel.

While only certain embodiments and examples of the present invention have been shown and described, it is obvious that many changes and modifications may be made thereunto without departing from the spirit and scope of the invention.

What is claimed is:

1. A process for measuring the calcium concentration of a biological fluid, comprising the steps of:
   (a) supplying a particular amount of phosphatidylcholine (PC) and phospholipase A2 (PLA) in the presence of a buffer and a detergent in a reaction mixture for enzymatic Reaction I,

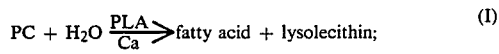

(b) measuring the rate of appearance of the products of Reaction I so that the reaction rate of PLA, being proportional to the concentration of calcium, is determined; and
   (c) comparing the reaction rate of PLA in Reaction I against the reaction rate of the same in, at least, one standard of known calcium concentration, thereby determining the calcium concentration of said biological fluid.

2. The process according to claim 1, wherein steps (b) and (c) are carried out by comparison of optical density of the resultant color in coupled Reactions II and III,

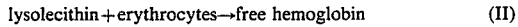

against, at least, one colorimetric standard of known calcium concentration, the optical density of the resultant color, as a function of time, being directly proportional with the calcium concentration of said biological fluid.

3. The process according to claim 2, wherein said colorimetric indicator is a member selected from the group consisting of pyrogallol, iodide, tetramethylbenzidine, benzidine, 4-aminoantipyrine+N,N-dimethylaniline, 4-aminoantipyrine+2,4-dichlorophenolsulfonic acid, and o-tolidine.

4. The process according to claim 2, wherein the optical density of the resultant color is measured by reflectance or transmission spectrophotometry.

5. The process according to claim 1, wherein the said biological fluid being tested is blood serum, blood plasma, whole blood, urine, saliva, cerebrospinal fluid, intestinal fluid, semen, amniotic fluid, synovial fluid, sweat, or peritoneal fluid.

6. The process according to claim 2, wherein the resultant color is measured by comparison with a color chart.

7. The process according to claim 2, wherein the erythrocytes are supplied either from a standardized exogenous source or from whole blood being tested.

8. A process for making a reaction mixture for measuring calcium concentration of a biological fluid, comprising the step of:
   supplying particular amounts of phospholipase A2 (PLA) and phosphatidylcholine (PC) in the presence of a buffer and a detergent in a reaction mixture for enzymatic Reaction I,

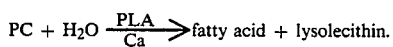
(I)

9. The reaction mixture for measuring the calcium concentration of a biological fluid made according to the process of claim 8.

10. A process for measuring the calcium concentration of a biological fluid for use in a paper phase, comprising the steps of:
    (a) supplying particular amounts of phospholipase A2(PLA) and phosphatidylcholine (PC), in the presence of a buffer and a detergent, in an aqueous mixture;
    (b) dipping a bibulous material into said aqueous mixture as in step (a);
    (c) removing said bibulous material from said aqueous mixture;
    (d) air-drying said bibulous material;
    (e) supplying particular amounts of indicator and peroxide in a miscible aqueous/organic mixture;
    (f) dipping a bibulous material into said aqueous/organic mixture as in step (e);
    (g) removing said bibulous material from said aqueous/organic mixture;
    (h) air-drying said bibulous material;
    (i) sandwiching a selectively permeable membrane of coating of a synthetic material or cellulose derivative between one each of the bibulous materials prepared as in steps (a–d) and (e–h);
    (j) applying said biological fluid and a supply of erythrocytes to the PLA/PC side of said sandwich prepared as in step (i) so as to initiate enzymatic Reaction I,

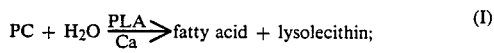
(I)

(k) measuring the rate of appearance of the products of Reaction I by the quantity of color produced on the indicator/peroxide side of the sandwich prepared as in step (i) in a quantitative colorimetric analysis;
    (l) comparing the quantity of color produced to, at least, one standard of known calcium concentration, whereby the quantity of color is directly proportional to the calcium concentration of said biological fluid being tested.

11. A process for making a bibulous material for measuring the calcium concentration of a biological fluid, comprising the steps of:
    (a) supplying particular amounts of phospholipase A2 and phosphatidylcholine, in the presence of a buffer and a detergent, in an aqueous mixture;
    (b) dipping a bibulous material into said aqueous mixture;
    (c) removing said bibulous material from said aqueous mixture;
    (d) air-drying said bibulous material;
    (e) supplying particular amounts of indicator and peroxide in an aqueous/organic mixture;
    (f) dipping a bibulous material into said aqueous/organic mixture as in step (e);
    (g) removing said bibulous material from said aqueous/organic mixture;
    (h) air-drying said bibulous material;
    (i) sandwiching a selectively permeable membrane or coating between one each of the impregnated bibulous materials prepared as in steps (a–d) and steps (e–h).

* * * * *